United States Patent [19]

Schapira et al.

[11] Patent Number: 5,374,607
[45] Date of Patent: Dec. 20, 1994

[54] PHYTOPHARMACEUTICAL WETTABLE POWDERS AND METHOD FOR THEIR PREPARATION

[75] Inventors: Joseph Schapira, Paris; Jacques Schild, Gennevilliers; Jacques Pecheur, Courbevoie; Ange C. Guerin, Le Plessis Bouchard; Dominique Ambrosi, Courbevoie; Jean-Jacques Fuchs, Deuil La Barre; Bernard Guyenet, Le Mesnil Le Roi, all of France

[73] Assignee: C F P I, France

[21] Appl. No.: 178,437

[22] Filed: Jan. 3, 1994

Related U.S. Application Data

[63] Continuation of Ser. No. 901,593, Jun. 19, 1992, abandoned.

[30] Foreign Application Priority Data

Jun. 20, 1991 [FR] France ............... 91 07592

[51] Int. Cl.$^5$ ............ A01N 37/34; A01N 43/707; A01N 43/82; A01N 43/34
[52] U.S. Cl. ............................. 504/310; 504/134; 504/146; 504/148; 504/149; 504/234; 504/263; 504/329; 504/330; 504/347; 71/DIG. 1
[58] Field of Search ......... 504/310, 234, 347, 330, 504/263, 329, 146, 149, 134, 148; 71/DIG. 1

[56] References Cited

U.S. PATENT DOCUMENTS

| | | | |
|---|---|---|---|
| 3,592,626 | 7/1971 | Heywood et al. | 71/70 |
| 3,796,562 | 3/1974 | Lamont et al. | 71/100 |
| 4,310,520 | 1/1982 | Narazaki | 71/88 |
| 4,376,113 | 3/1983 | Suglia et al. | 71/DIG. 1 |
| 4,813,999 | 3/1989 | Schapira et al. | 71/105 |

FOREIGN PATENT DOCUMENTS 995383  6/1965  United Kingdom .

Primary Examiner—Allen J. Robinson
Assistant Examiner—Deborah Lambkin
Attorney, Agent, or Firm—Larson and Taylor

[57] ABSTRACT

Phytopharmaceutical wettable powder comprising at least one phytopharmaceutical active substance which is solid at ambient temperature and at least one pulverulent inert filler, characterized by the fact that the constitutive particles of the filler constitute a support or carrier for the active substance comprised within a liquid composition, said active substance being selected from the group comprising:

the esters of the family of the parahydroxybenzonitriles of the group comprising bromoxynil octanoate, bromoxynil heptanoate, bromoxynil butyrate, ioxynil octanoate, ioxynil heptanoate, ioxynil butyrate, the triazines of the group comprising simazine, atrazine and ametryne, the dinitroanilines of the group comprising butraline, pendimethaline, trifluraline, orizaline, the substituted ureas of the group comprising diuron, isoproturon, ethidimuron, the sulphonylureas of the group comprising especially chlorsulfuron.

10 Claims, No Drawings

1

PHYTOPHARMACEUTICAL WETTABLE POWDERS AND METHOD FOR THEIR PREPARATION

This application is a continuation of application Ser. No. 07/901,593 filed Jun. 19, 1992, abandoned.

The present invention relates to phytopharmaceutical wettable powders comprising at least one active phytopharmaceutical substance which is solid at ambient temperature.

It also relates to a method for manufacture of the said powders.

By the expression "wettable powder" are meant pulverulent matters which, when mixed with water, provide stable suspensions.

These suspensions are called "spray-mixtures".

Phytopharmaceutical wettable powders comprising in powder form, in mixture, at least one phytopharmaceutical active substance solid at ambient temperature as well as an inert filler are already known.

These phytopharmaceutical wettable powders are manufactured using so-called powder grinders, for instance those which are sold by the Company FORPLEX, and with which the phytopharmaceutical active solid substance is brought to a sufficient low degree of division or particle size; the drawback which is inherent to the use of these grinders comes from the fact that, for reasons of protection of the environment, it is necessary to filtrate the large volumes of air which are necessary for their running.

This drawback is still increased when compressed air mills are used, which are called "jet-mill", and which it is necessary to use when a particle size or size-grading smaller than that obtained with the above-mentioned powder grinders is contemplated.

It has already been proposed to overcome the drawbacks of the above-mentioned powder grinders by adjustment of the latter in such a way that the emission of dust is decreased, but then the grinding is more coarse and provides a less good stability of the "spray-mixture", i.e. the diluted form in water under which they are used, the consequence of the resulting quick deposition being a heterogeneous biological treatment.

A further drawback of the phytopharmaceutical wettable powders which are already known is that a certain number of active substances may be difficult to be ground, either because they are too hard, or because, while being solid, they show a plastic behaviour, or again because a softening occurs during grinding, or again because they have a melting point which is sufficiently low to be reached during grinding.

Finally, the wettable powders which are already known and which are obtained by dry grinding of their various constitutive compounds may present some cutaneous toxicity with respect to the worker or the user, due to the fact that the finely divided active substances which are part of the powders may come in direct contact with the skin.

The object of the invention is, above all, to overcome the drawbacks of the wettable powders of the prior art, i.e. essentially their toxicity as well as the pollution occuring during their manufacture.

Now, Applicants have had the merit of having found that, in an unexpected and surprising manner, not only the said object is reached provided the phytopharmaceutical active substance which is solid at ambient temperature and which is selected from the group comprising:

the esters of the family of the parahydroxybenzonitriles of the group comprising bromoxynil octanoate, bromoxynil heptanoate, bromoxynil butyrate, ioxynil octanoate, ioxynil heptanoate, ioxynil butyrate, the triazines of the group comprising simazine, atrazine and ametryne, the dinitroanilines of the group comprising butraline, pendimethaline, trifluraline, orizaline, the substituted ureas of the group comprising diuron, isoproturon, ethidimuron, the sulphonylureas of the group comprising especially chlorsulfuron, is present within the wettable powder in the form a liquid phytopharmaceutical composition obtained by liquifying the said active substance by means of certain mineral and/or organic solvents, some of which are themselves active substances, and/or by means of surfactive agents and/or by mixture with another active substance proper to form with the phytopharmaceutical substance a liquid phase, especially an eutectic, but furthermore the thus obtained wettable powder has a biological activity improved with respect to the biological activity of the phytopharmaceutical wettable powders according to the prior art.

This improvement of the biological activity is consisting not only of a better selectivity and/or a better efficiency of the wettable powders according to the invention, but also in the enlargement of the possibilities of use of the said powders, especially from the point of view of the moment of their use, of the vegetative slade of the vegetables to be treated and of the various climatic conditions.

Consequently, the phytopharmaceutical wettable powder according to the invention which comprises at least one phytopharmaceutical active substance which is solid at ambient temperature and at least one pulverulent inert filler, is characterized by the fact that the constitutive particles of the filler constitute a support or carrier for the active substance comprised within a liquid composition, said active substance being selected from the group comprising:

the esters of the family of the parahydroxybenzonitriles of the group comprising bromoxynil octanoate, bromoxynil heptanoate, bromoxynil butyrate, ioxynil octanoate, ioxynil heptanoate, ioxynil butyrate, the triazines of the group comprising simazine, atrazine and ametryne, the dinitroanilines of the group comprising butraline, pendimethaline, trifluraline, orizaline, the substituted ureas of the group comprising diuron, isoproturon, ethidimuron, the sulphonylureas of the group comprising especially chlorsulfuron.

The said liquid composition is obtained by liquifying the phytopharmaceutical active substance:

a) by means of a solvent selected from the group comprising aliphatic, aromatic, cycloaliphatic mineral oils, solvents of petroleum origin of the alkylaromatic type, plant oils, dimethylformamide, dimethylsulphoxide, dimethylacetamide, N-methylpyrrolidone, dimethylimidazolinone, hexamethylene-phosphotriamide, cyclohexanone, acetophenone, alcohol diacetone, butylbenzylphthalate, dialkylphthalates, short alcohols with a chain in $C_1$ to $C_8$ and their oxyethylenated and/or oxypropylenated derivatives, ethyleneglycol, propyleneglycol, and the solvents on the basis of alkylbenzene and alkylnaphthalene, in which the alkyl chain comprises from 1 to 8 carbon atoms, and/or b) by means of a liquid active substance selected from the group comprising, on the one hand, the phenoxyacids, especially 4- and 3-chlorophenoxyacetic acid, 2.4-D, MCPA, mecoprop and dichlorprop as well as their dextrogyre isomers, in the form of esters of the group comprising those of butyglycol, 2-ethylhexanol, isooctanol and of the alcohols in $C_8$, on the other hand the fluazifop-butyl, metolachlor, pretilachlor, sethoxydime, tebutame, and/or c) by means of a surfactive agent selected from the group comprising:

non-ionic surfactive agents obtained by reaction of ethylene and/or propylene oxide on fatty alcohols, alkylphenols, tristyrylphenols, fatty amides, fatty amines, anionic surfactive agents which are the sulphonated, sulphated or phosphorated derivatives of the above-mentioned non-ionic surfactive agents, possibly neutralized by aliphatic amines, alkanolamines or sodium or potassium hydroxide, calcium dodecylbenzenesulphonate, calcium alkylbenzenesulphonates having a alkyl chain in $C_{12}$ to $C_{18}$, sodium or calcium alkylnaphthalenesulphonates, sodium, calcium or ammonium lignosulphonates, formol/cresol/ betanaphtholsulphonate condensates and/or d) by mixture with a solid active substance proper to form with it an eutectic, the corresponding combination being selected from the group comprising:

the combination of bromoxynil octanoate with bromoxynil butyrate, the proportions being respectively 60% and 40% by weight, the melting point being 25° C., the combination of bromoxynil heptanoate with bromoxynil butyrate, the proportions being respectively 70% and 30% by weight, the melting point being 26° C., the combination of bromoxynil octanoate with bromoxynil heptanoate, the proportions being respectively 50% and 50% by weight, the melting point being 26° C.

The above-mentioned solvents on the basis of alkylbenzene and alkylnaphtalene may be selected from those known under the trademarks SHELL SOL R ®, SOLVESSO 200 ® and NAPHTA ® commericialized respectively by the Companies SHELL, ESSO or EXXON and TOTAL.

Within the above-mentioned liquid composition, the solvent and/or the liquid active substance selected for liquifying are present in an amount of at most 50% by weight and preferably of at most 25% by weight, the surfactive agent being present in a proportion of at most 20% by weight and preferably in a proportion of 5 to 10% by weight with respect to the total weight of the liquid composition.

The process for the preparation of the phytopharmaceutical wettable powder according to the invention is characterized by the fact that there is prepared a liquid composition by liquifying at least one phytopharmaceutical active solid substance of the above-identified group, by means of a solvent and/or by means of a liquid active substance and/or by means of a surfactive agent and/or by formation of an eutectic with another solid active substance of the group hereabove defined, the said liquid composition being applied on the constitutive particles of an inert pulverulent filler.

A special advantage of the process according to the invention is that the active substance(s) are distributed in a homogeneous manner within the said powder, which is especially advantageous when, in the event that several active substances are used, one of the said substances is present in an amount very lower than that of the other active substances.

Every possible combination of the active substances selected as per the invention can be contemplated in order to constitute the wettable powders according to the invention.

These powders comprise from 1 to 50% by weight and preferably from 10 to 25% by weight of at least one of the above-mentioned phytopharmaceutical active substances.

The pulverulent inert filler which constitutes the carrier of the phytopharmaceutical active substance comprised within the said liquid composition can be selected from the group comprising silica and clays.

Illustrative examples of carriers are those known under the trademarks TIX-O-SIL 38 ® and ARGIREC B 22 ®, respectively commericialized by RHÔNE-POULENC and BLANC MINERAUX DE PARIS.

The phytopharmaceutical wettable powder according to the invention comprises from 30 to 95% by weight of at least one pulverulent carrier with respect to the total weight.

According to an advantageous embodiment of the process according to the invention for the preparation of the phytopharmaceutical wettable powder, the above-mentioned liquid composition is slowly poured on the pulverulent inert filler which constitutes an absorbent carrier which is stirred in a powder mixer.

The powder mixers which are adapted to be used in the process or method according to the invention may consist of horizontal drums equipped with paddles, by belt-, impeller-, screw-, discs- or sockets-mixers, or by any other device allowing the mixture of powders.

By way of examples, the devices known under the trademarks MYERS ®, VIDAX ®, SEVIN ®, LODIGE ®, TURBOSPHERE ® can be used.

The output of the liquid composition which is poured or sprayed on the inert filler, the speed of stirring of the carrier as well as the respective proportions of the liquid composition and of the filler are adjusted in such a way that there is obtained a homogeneous wettable powder which flows easily.

The homogeneity of the wettable powder can be evaluated visually or measured on samples.

As soon as the totality of the liquid composition has been absorbed on the inert filler, the wettable powder thus obtained contains few or no agglomerates and the walls of the mixing device are clean.

It is possible to add to the sand wettable powder wetting agents, dispersing agents and surfactive agents; for example, it is possible to add by spraying a liquid surfactive agent playing an anti-dust role or by dusting of a surfactive agent which is solid; it is also possible to add to the said wettable powder further active substances in the form of powder of the group comprising amino-triazole and the sodium, potassium and/or magnesium salts of phenoxyacids such as mecoprop, these active substances having to be soluble in water at the dose of use of the final wettable powder on the plants; it is also possible to add a "conventional" wettable powder, that is to say a wettable powder obtained by dry grinding of its various constituents.

The thus obtained mixture is stirred until obtention of the requested homogeneity.

A particular advantage of the process of preparation according to the invention of the phytopharmaceutical wettable powder is that it does not necessitate any drying, the consequence being a simplification and a reduction of the cost of the wettable powder.

The following examples which permit to better understand the invention are not limitative and are given for illustrative reason with reference to preferred advantageous embodiments.

EXAMPLE 1

A wettable powder according to the invention on the basis of bromoxynil octanoate is prepared, the proportion of the said active substance within the wettable powder being 20% by weight.

Inside a heating mixing device, 30.7 parts by weight of bromoxynil octanoate containing 65.3% of active substance are dissolved in a mixture of 2.5 parts by weight of an emulsifying agent known under the trademark GALORYL EM 514 ®, 6 parts by weight of an emulsifying agent known under the trademark GALORYL EM 60 ® and 10.8 parts by weight of a solvent of petroleum origin.

The emulsifying agents known under the trademark GALORYL EM consist of non-ionic surface active agents of the fatty alcohol type or of the type corresponding to polyethoxylated castor oil, these agents being possibly used together with calcium dodecylbenzenesulfonate.

The solubilization of the bromoxynil octanoate can be improved by a light heating to 40°-50° C.

A homogenous liquid is obtained.

The thus obtained solution is applied inside a mixing device which may be one of those sold by the Company MYERS, on 41 parts by weight of a silica known under the trademark TIX-O-SIL 38 ®; inside the said mixing device, 1 part by weight of a wetting agent known under the trademark GALORYL MT 41182 ® (non-ionic wetting agent on the basis of alkylarylsulfonates and lignosulfonates) and 8 parts by weight of a dispersing agent known under the trademark GALORYL DT 201 ® (a polymer of hydroxynaphthalene sodium sulfonate and of methylphenol); are added.

The mixture is homogenized.

A beige colour powder having a particle size lower than 250 μm (standard AFNOR N° 25) is obtained; the wettability of the said powder in hard water (according to the standard OMS, introduction of 1 gram of powder into 100 ml of water) is from 30 to 40 seconds at most and its suspensivity (type FISHER, hard water OMS, introduction of 10 grams of powder into 1 liter of water, 15 turns-up and then standing during 30 minutes) is 80% at least.

This powder has the following centesimal composition:

| | |
|---|---|
| Bromoxynil octanoate (containing 65.3% of a.s.) | 30.7 |
| Emulsifying agent of the trademark GALORYL EM 514 ® | 2.5 |
| Emulsifying agent of the trademark GALORYL EM 60 ® | 6.0 |
| Solvent of petroleum origin | 10.8 |
| TIX-O-SIL 38 ® | 41.0 |
| Wetting agent (GALORYL MT 41182) | 1.0 |
| GALORYL DT 201 ® | 8.0 |
| | 100.0 |

EXAMPLE 2

A wettage powder according to the invention is prepared on the basis of 10% by weight of bromoxynil in the form of octanoate and 10% by weight of bromoxynil in the form of heptanoate.

Inside a heating mixing device, there are dissolved at ambient temperature 15.4 parts by weight of bromoxynil octanoate containing 65.3% of active substance, and 14.9 parts by weight of bromoxynil heptanoate containing 67.4% of active substance in a mixture of 3.1 parts by weight of emulsifying agent known under the trademark GALORYL EM 514 ®, 5.7 parts by weight of emulsifying agent known under the trademark GALORYL EM 60 ®, and 10.9 parts by weight of a solvent of petroleum origin.

The solubilization of the bromoxynil octanoate and of the bromoxynil heptanoate can be improved by a light heating to 40°-50° C.

There is obtained a homogeneous transparent liquid.

The thus obtained solution is applied inside a mixer which may be selected among those commercialized by the Company MYERS, onto 41 parts by weight of a silica of the trademark TIX-O-SIL 38 ®; inside the said mixture there are added 1 part by weight of wetting agent known under the trademark GALORYL MT 41182 ® and 8 parts by weight of a dispersing agent known under the trademark GALORYL DT201 ®.

The mixture is homogenized.

A beige colour powder having a particle size lower than 250 μm (standard AFNOR N° 25) is obtained, the wettability of the said powder in hard water (according to the standard OMS, introduction of 1 gram of powder into 100 ml of water) is from 30 to 40 seconds at most and its suspensivity (type FISHER, hard water OMS, introduction of 10 grams of powder into 1 liter of water, 15 turns-up and then standing during 30 minutes) is 80% at least.

The thus obtained powder has the following centesimal composition:

| | |
|---|---|
| Bromoxynil octanoate (containing 65.3% of a.s.) | 15.4 |
| Bromoxynil heptanoate (containing 67.4% of a.s.) | 14.9 |
| Emulsifying agent of the trademark GALORYL EM 514 ® | 3.1 |
| Emulsifying agent of the trademark GALORYL EM 60 ® | 5.7 |
| Solvent of petroleum origin | 10.9 |
| TIX-O-SIL 38 ® | 41.0 |
| Wetting agent (GALORYL MT 41182) | 1.0 |
| GALORYL DT 201 ® | 8.0 |
| | 100.0 |

EXAMPLE 3

This example, as a comparative example intended to show the superiority of the wettable powders according to the invention with respect of those of the prior art, consists in the comparison of tests in green houses, illustrated by Table I hereabove:
 on the one hand, the wettable powder according to the invention disclosed in example 1 and on the other hand, a wettable powder corresponding to the prior art, called powder A, whose composition is indicated hereafter and which is different from the powder according to the invention by the fact that it does not comprise an intermediate liquid composition obtained by means of a solvent, the solvent being substituted by an equivalent quantity of silica.

The phytopharmaceutical active substance of powder A corresponding to the prior art is consisting of bromoxynil octanoate whose content in active substance is 65.3% by weight.

Except the fact that the application of the active substance on the pulverulent inert carrier necessitated, as far as powder A is concerned, a heating of the active substance of the filler and of the device to 40°-50° C., the conditions of manufacture of the said powder A are the same as those disclosed for the preparation of the wettable powder according to the invention disclosed in example 1.

Powder A thus obtained has the following centisomal composition:

| | |
|---|---|
| Bromoxynil octanoate (containing 65.3% of a.s.) | 30.70 |
| Emulsifying agent of the trademark GALORYL EM 514 ® | 2.50 |
| Emulsifying agent of the trademark GALORYL EM 60 ® | 6.00 |
| Solvent of petroleum origin | 0.00 |
| TIX-O-SIL 38 ® | 51.80 |
| Wetting agent (GALORYL MT 41182) | 1.00 |
| GALORYL DT 201 ® | 8.00 |
| | 100.00 |

Concerning these two wettable powders, determination was made of the percentages of the destruction of the weeds quoted in the first column of Table I 21 days after the application using, in connection with three successive tests, respectively three doses of active substance per hectare, that is to say 50 grams/hectare, 100 grams/hectare and 200 grams/hectare.

TABLE I

| | Wettable powder according to the invention (example 1) | | | Wettable powder according to the prior art (powder A) | | |
|---|---|---|---|---|---|---|
| | Doses in a.s.* (g/ha) | | | | | |
| Treated weeds | 50 | 100 | 200 | 50 | 100 | 200 |
| | Destruction (in %) | | | | | |
| Ambrosia | 45 | 55 | 95 | 5 | 15 | 50 |
| Chenopodium | 0 | 3 | 95 | 3 | 5 | 13 |
| Daucus | 0 | 0 | 3 | 0 | 0 | 0 |
| Galium | 15 | 35 | 85 | 5 | 25 | 45 |
| Matricaria | 18 | 83 | 100 | 0 | 10 | 70 |
| Rumex | 0 | 10 | 15 | 3 | 8 | 20 |
| Solanum | 95 | 100 | 100 | 55 | 88 | 98 |
| Stellaria | 5 | 5 | 5 | 3 | 3 | 5 |
| Taraxacum | 8 | 45 | 80 | 5 | 5 | 10 |
| Veronica | 30 | 100 | 100 | 10 | 95 | 98 |
| Average | 22 | 44 | 68 | 9 | 25 | 41 |

*a.s. = active substance

The results of these tests collected in Table I show that, at the dose of 50 grams/hectare, there is obtained an average percentage of destruction equal to 22% in the case of the wettable powder according to the invention compared with an average percentage of destruction equal to 9% in the case of the wettable powder (A) according to the prior art; at the dose of 100 grams/hectare, the destruction is respectively 44% and 25% and, at the dose of 200 grams/hectare, the said weight of destruction is 68% and 41% respectively.

EXAMPLE 4

A wettable powder according to the invention is prepared on basis of 6% by weight of ioxynil in the form of octanoate, 6% by weight of ioxynil in the form of heptanoate and 18% by weight of dextrogyre mecoprop (MCPP) in the form of butylglycol ester (BG).

Inside a heating mixing device, there are dissolved at ambient temperature 8.45 parts by weight of ioxynil octanoate containing 71.1% of active substance, 8.20 parts by weight of ioxynil heptanoate containing 73.3% of active substance in a mixture comprising 27.70 parts by weight of dextrogyre MCPP BG ester containing 67.4% of active substance, 2.25 parts by weight of an emulsifying agent of the trademark GALORYL EM 514 ®, 2.75 parts by weight of an emulsifying agent of the trademark GALORYL EM 60 ®, and 0.65 part by weight of a solvent of petroleum origin.

The solubilization of the active substances can be improved by a light heating to 40°-50° C.

A homogeneous transparent liquid is obtained.

The thus obtained solution is applied inside a mixer which may be one of those commercialized by the Company MYERS, on 41 parts by weight of a silica of the trademark TIX-O-SIL 38 ®; there is added inside the said mixer 1 part by weight of a wetting agent known under the trademark GALORYL MT 41182 ® and 8 parts by weight of a dispersing agent known under the trademark GALORYL DT 201 ®.

The mixture is homogenized inside the said mixer.

The thus obtained beige colour powder of a particle size lower than 250 μm (standard AFNOR N° 25) whose the wettability in hard water (according to the standard OMS, introduction of 1 gram of powder into 100 ml of water) is from 30 to 40 seconds at most and whose suspensivity (type FISHER, hard water OMS, introduction of 10 grams of powder into 1 liter of water, 15 turns-up and then standing during 30 minutes) is 65% at least.

The thus obtained powder has the following centesimal composition:

| | |
|---|---|
| Ioxynil octanoate (containing 71.1% of a.s.) | 8.45 |
| Ioxynil heptanoate (containing 73.3% of a.s.) | 8.20 |
| MCPP Dextrogyre Ester BG (containing 67.4% of a.s.) | 27.70 |
| Emulsifying agent of the trademark GALORYL EM 514 ® | 2.25 |
| Emulsifying agent of the trademark GALORYL EM 60 ® | 2.75 |
| Solvent of petroleum origin | 0.65 |
| TIX-O-SIL 38 ® | 41.00 |
| Wetting agent (GALORYL MT 41182) | 1.00 |
| GALORYL DT 201 ® | 8.00 |
| | 100.00 |

EXAMPLE 5

A wettable powder according to the invention on the basis of 25% by weight of butraline is prepared.

Inside a heating mixing device, there is dissolved at ambient temperature 25.65 parts by weight of butraline having a purity of 97.5% in a mixture comprising 5 parts by weight of a surfactive agent of the trademark GALORYL EM 458 ®, 5 parts by weight of a surfactive agent of the trademark GALORYL MT 41 ® and 14.35 parts by weight of a solvent of petroleum origin.

The solubilization of butraline can be promoted by a light heating to 45°-50° C.

It is thus obtained a homogeneous transparent liquid.

The thus obtained solution is applied inside a mixer which can be selected among those commercialized by the Company MYERS, on 41 parts by weight of a silica of the trademark TIX-O-SIL 38 ®; still inside the same mixer, there are added 1 part by weight of a wetting agent of the trademark GALORYL MT 41182 ® and 8 parts by weight of a dispersing agent of the trademark GALORYL DT 201 ®.

The mixture is homogenized inside the mixer.

It is thus obtained a yellow powder of particle size lower than 200 μm whose wettability in hard water (according to the standard OMS, introduction of 1 gram of powder into 100 ml of water) is at most 1 minute.

The thus obtained powder has the following centesimal composition:

| | |
|---|---|
| Technic butraline (purity = 97.5%) | 25.65 |
| GALORYL EM 458 ® | 5.00 |
| GALORYL MT 41 ® | 5.00 |
| Solvent of petroleum origin | 14.35 |
| TIX-O-SIL 38 ® | 41.00 |
| Wetting agent (GALORYL MT 41182) | 1.00 |
| GALORYL DT 201 ® | 8.00 |
| | 100.00 |

EXAMPLE 6

A wettable powder according to the invention on the basis of 13% by weight of bromoxynil in the form of octanoate and 26% by weight of dextrogyre mecoprop in the form of magnesium salt is prepared.

The preparation of the said wettable powder according to the invention is consisting in the mixture of two wettable powders which are prepared independently of one another.

One of these two wettable powders is the one of example 1, the other wettable powder, which is called powder B, is on the basis of 75% by weight of dextrogyre mecoprop in the form of magnesium salt.

Powder B is prepared by mixing, inside a powder mixer of the trademark LODIGE, 93.75 parts by weight of dextrogyre mecoprop in the form of magnesium salt having a content in active substance of 80%, 1 part by weight of a dispersing agent of the trademark GALORYL MT 41182 ®, 2 parts of a dispersing agent of the trademark GALORYL DT 201 ® and 3.25 parts by weight of a silica of the trademark TIX-O-SIL 38 ®.

The thus obtained powder B has the following centesimal composition:

| | |
|---|---|
| Dextrogyre mecoprop in the form of magnesium salt | 93.75 |
| GALORYL MT 41182 ® | 1.00 |
| GALORYL DT 201 ® | 2.00 |
| TIX-O-SIL 38 ® | 3.25 |
| | 100.00 |

The wettable powder on the basis of bromoxynil octanoate and of dextrogyre mecoprop in the form of magnesium salt is obtained by mixing 65 parts by weight of the wettable powder according to example 1, 34.6 parts by weight of powder B and 0.4 part by weight of a silica of the trademark TIX-O-SIL 38 ®; its centisemal composition is as follows:

| | |
|---|---|
| Wettable powder according to example 1 | 65.0% |
| Powder B | 34.6% |
| TIX-O-SIL 38 ® | 0.4% |
| | 100.0% |

EXAMPLE 7

Comparative tests in "field crops" have been carried out.

In order to check the biological activity of phytopharmaceutical wettable powders according to the invention, the following products were compared:

a concentrated aqueous suspension of bromoxynil phenol containing 250 grams/liter of active substance (I), an emulsifiable concentrate of bromoxynil octanoate containing 240 grams/liter of active substance (II), the wettable powder according to example 1 containing bromoxynil octanoate at a proportion of 20% of active substance (III), the wettable powder according to example 2 containing bromoxynil octanoate and heptanoate respectively each of them at a proportion of 10% by weight, which means 20% of active substance in a whole (IV), a wettable powder prepared according to the prior art and containing bromoxynil octanoate at a proportion of 20% by weight of active substance (V).

The products I and II are commercial products according to the prior art whose biological activities are well known with respect to corn on the level of their phytotoxicity, as well as on the level of herbicidal efficiency with respect to usual weeds in corn crops, these plants which are difficult to be destroyed being Chenopodes and Amarantes.

For the products I to V, the herbicidal efficiency with respect to the same Chenopodes and Amarantes as well as their selectivity with respect to corn was measured.

The useful and necessary doses at which the said products have been applied are determined as a function of an efficiency level of at least 80% of destruction and, if possible, close to 90% as a function of the selectivity.

The said doses are indicated hereafter:

as far as product I is concerned, the average dose is 600 grams of active substance/hectare within a practical range from 450 to 750 grams of active substance/hectare, as far as product II is concerned, the average useful dose is 350 grams of active substance/hectare in order to be close to acceptable efficiency levels, as far as products III and IV are concerned, the average useful dose is 450 grams of active substance/hectare in order to be close to acceptable efficiency levels, as far as product V is concerned, the average useful dose is 600 grams of active substance/hectare.

Each treatment is applied on two elementary experimental plots A and B located in three different fields. Each plot comprises 3 raws of corn plant of a surface equal to 2.40 meters×10 meters=24 m$^2$.

The application of the products is carried out when the corn is at the stage from 4 to 6 leaves, and when the weeds are between the stages of 2 cotyledon leaves and from 4 to 6 true leaves.

The application of the different products is carried out by normal spray at a rate of 250 liters of spray-mixture per hectare. Each product (I to V) has been applied at the rate of 2 doses of active substance/hectare; the underlined dose in Table II corresponds to recommended dose of use.

Fifteen days after the treatment, there was observed:
- on the one hand the phytotoxicity on corn, the phytotoxicity being appreciated as an average percentage of necrosed leave surface,
- on the other hand the efficiency which is appreciated as a percentage of destroyed weeds.

The results of these observations are collected in Table II.

From these results, it is possible to conclude that the wettable powders according to the invention, while having a general effect clearly better than concentrated suspension and emulsifiable concentrate, are hardly more phytotoxic as the conventional wettable powder and are significantly more efficient than the latter while having a content in active substance/hectare clearly lower.

As indicated in example 7, the phytotoxicity has been examined at two times, namely at time T=10 days and at time T=15 days.

The average percentages of necrosed leave surface as well as the whole data are collected in Table III.

TABLE III

| Active substance content (a.s.) | I Concentrated suspension of bromoxynil phenol 250 g/l | | II Emulsifiable concentrate of bromoxynil octanoate 240 g/l | | III Wettable powder according to the invention of bromoxynil octanoate (example 1) 20% | | IV IV-A Aqueous solution of bromoxynil diethanolamine salt 360 g/l | | V Conventional wettable powder of bromoxynil octanoate 20% | |
|---|---|---|---|---|---|---|---|---|---|---|
| Dose of a.s. (g/ha) | 600 | 1200 | 225 | 450 | 450 | 900 | 600 | 1200 | 900 | 1800 |
| Results (%) (phytotoxicity) | C D | C D | C D | C D | C D | C D | C D | C D | C D | C D |
| T = 10 days | 5 4 | 10 8 | 11 15 | 24 28 | 1 2 | 3 6 | 7 5 | 10 8 | 2 2 | 6 3 |
| T = 15 days | 5 9 | 10 11 | 11 18 | 24 38 | 1 5 | 4 9 | 7 8 | 10 10 | 2 6 | 10 9 |

From the examination of Table III, it appears that, while having the same efficiency, the wettable powder according to the invention shows a phytotoxicity against corn better or comparable to that of a conventional wettable powder, the dose of active substance being twice lower per hectare, this is an improvement from the economical point of view as well as from the point of view of environmental protection, a better advantage being taken of the active substance. Furthermore, the wettable powder according to the invention provides a very great security for corn in case of overdose with respect to the existing formulations of the emulsifiable concentrate type, of the aqueous solution type, or of the concentrated suspension type.

EXAMPLE 9

A wettable powder according to the invention and a conventional wettable powder are prepared from a triazine, namely ametryne.

a) Preparation of wettable powder according to the invention.
  1. 21.35 parts by weight of a solvent of petroleum origin SHELL SOL ®,
  2. 2.60 parts by weight of N-methyl-pyrrolidone as solvent,
  3. 3.15 parts by weight of NANSA EVM 70 i ® as surfactive agent,

TABLE II

| Active substance content (a.s.) | I Concentrated suspension of bromoxynil phenol 250 g/l | | II Emulsifiable concentrate of bromoxynil octanoate 240 g/l | | III Wettable powder according to the invention of bromoxynil octanoate (example 1) 20% | | IV Wettable powder according to the invention of bromoxynil octanoate/heptanoate (example 2) 20% | | V Classical wettable powder of bromoxynil octanoate 20% | |
|---|---|---|---|---|---|---|---|---|---|---|
| Dose of a.s. (g/ha) | 450 | 600 | 225 | 350 | 350 | 450 | 350 | 450 | 450 | 600 |
| Selectivity | A B | A B | A B | A B | A B | A B | A B | A B | A B | A B |
| Field 1 | 0 0 | 0 0 | 5 0 | 30 30 | 2.5 0 | 0 0 | 0 0 | 0 0 | 0 0 | 0 0 |
| Field 2 | 5 15 | 15 5 | 5 5 | 5 30 | 2.5 0 | 2.5 5 | 2.5 0 | 5 5 | 0 0 | 0 0 |
| Field 3 | 5 5 | 5 15 | 15 5 | 15 30 | 2.5 2.5 | 5 2.5 | 2.5 0 | 2.5 0 | 0 0 | 0 0 |
| Average Efficiency | 5 | 8.3 | 5.8 | 23.3 | 2.5 | 2.5 | 0.8 | 2 | 0 | 0 |
| Amarante* | 65 | 85 | 78 | 83 | 94 | 94 | 93 | 95 | 86 | 90.8 |
| Chenopole* | 61 | 89 | 87 | 80 | 90 | 96 | 82 | 94 | 80 | 80 |

*Plants to be destroyed.

EXAMPLE 8

The phytotoxicity against corn of the products tested in example 7, except product IV of example 7 which has been replaced by product IV-A constituted by an aqueous solution of bromoxynil diethanolamine salt, has been studied.

The different products have been applied under the form of two doses on two different plots C and D.

2.60 parts by weight of an emulsifying agent GALORYL EM 33 ®, are mixed, then 10.30 parts by weight of technic ametryne (purity 98%) are added and the complete solubilization is obtained by heating to 40°-50° C.

The mixture is absorbed on:

51 parts by weight of a carrier TIX-O-SIL 38 ® and then, after homogenization, 1 part by weight of a wetting agent GALORYL MT 41182 ® and 8 parts by weight of a dispersing agent GALORYL DT 201 ® are added.

Crushing is carried out in a grinder equipped with a 1-2 mm grid.

A beige colour powder is obtained; its particle size is lower than 200 μm and its wettability in hard water OMS, introduction of 1 g of powder into 100 ml of water, is from 30 seconds at most.

b) Preparation of a conventional wettable powder.

The following constituents are intimately mixed:

| Technic ametryne (purity 98%) | 81.6 |
| ARGIREC B 22 ® as clay | 8.4 |
| GALORYL MT 41182 ® as a wetting agent | 3.0 |
| GALORYL DT 201 ® as a dispersing agent | 7.0 |
| | 100.0 |

An intimate mixing is performed in a grinder equipped with a 0.5 mm grid.

The thus obtained beige colour powder has a particle size lower than 100 μm and a wettability in hard water OMS, introduction of 1 g of powder in 100 ml of water, of 1 minute at most.

c) Comparative test in "pre-emergence".

The two powders have been applied at the rate of 1000, 2000 and 3000 g/ha of active substance by spraying a spray-mixture at the dose of 500 l/ha on earthenwares (terrines) of 10×20 cm in which dicotyledon weed species are sawn.

The results recorded in Table V have been collected 28 days after the seeding and the treatment; said results are expressed in percentages of destruction with respect to the non treated plants taken as control:

TABLEAU IV

| Wettable powder | according to the invention | | | conventional | | |
|---|---|---|---|---|---|---|
| Doses of ametryne (g/ha) | 1000 | 2000 | 3000 | 1000 | 2000 | 3000 |
| % of destruction on Solanum nigrum | 60 | 73 | 85 | 50 | 50 | 55 |

Thus, the wettable powder according to the invention shows a very clear superiority, even in pre-emergence, with respect to the conventional wettable powder.

d) The two powders have been applied at the rate of 1000, 2000 and 3000 g/ha of active substance by spraying of a spray-mixture at the dose of 500 l/ha, on earthenwares of 10×20 cm in which different gramineous weed species have been sawn 15 to 20 days before.

The results recorded in Table V have been collected 10 days after the treatment; said results are expressed in percentages of destruction with respect to non treated plants taken as control.

TABLEAU IV

| Wettable powder | according to the invention | | | conventional | | |
|---|---|---|---|---|---|---|
| Doses of ametryne (g/ha) | 1000 | 2000 | 3000 | 1000 | 2000 | 3000 |
| % of destruction on | | | | | | |
| Digitaria | 20 | 35 | 45 | 10 | 10 | 20 |
| Echinochloa | 20 | 25 | 35 | 5 | 8 | 10 |
| Setaria | 70 | 90 | 100 | 35 | 50 | 80 |

The wettable powder according to the invention shows a very clear superiority with respect to a conventional wettable powder.

EXAMPLE 10

A comparative study of the "biological" properties of the wettable powder according to the invention disclosed in Example 5 (Powder K) has been carried out with the properties of a conventional wettable powder (Powder L) prepared as indicated hereafter and the properties of a wettable powder (Powder M) identical to Powder K, except the fact that the solvent of petroleum origin is replaced by silica, this Powder M being prepared as indicated hereafter.

a) Preparation of Powder L.

25.65 parts by weight of technic butraline having a purity of 97.5% have been melt and poured on 65.35 parts by weight of a carrier constituted by silica of trademark TIX-O-SIL 38 ® until complete absorption.

1 part of weight of a wetting agent of trademark GALORYL MT 41182 ® and 8 parts by weight of a dispersing agent of trademark GALORYL DT 201 ® are then added.

The mixture is homogenized and crushed in a grinder equipped with a 1 mm grid.

The thus obtained yellow powder of particle size lower than 200 μm has a wettability in hard water OMS (introduction of 1 g of powder in 100 ml of water) from 2 to 3 minutes.

b) Preparation of Powder M.

25.65 parts by weight of technic butraline having a purity of 97.5% have been melt and poured on 55.35 parts by weight of a carrier consisting of silica of trademark TIX-O-SIL 38 ® until complete absorption.

The mixture is then absorbed on 5 parts by weight of a surfactive agent of trademark GALORYL EM 458 ® and 5 parts by weight of a surfactive agent of trademark GALORYL MT 41 ®.

This mixture is homogenized and 1 part by weight of a wetting agent of trademark GALORYL MT 41182 ® and 8 parts by weight of a dispersing agent of trademark GALORYL DT 201 ® are added.

The mixture is homogenized inside the mixer and crushed in a grinder equipped with a 1 mm grid.

A yellow powder of particle size lower than 200 μm is obtained; its wettability in hard water OMS (introduction of 1 g of powder in 100 ml of water) is at most 1 minute.

A comparative test disclosed hereafter is carried out using these three powders.

Each one of powders K, L and M has been applied at the rate of 1000 and 3000 g/ha of active substance (butraline) by spraying of a spray-mixture at the dose of 500 l/ha on earthenwares of 10×20 cm in which different gramineous and dicotyledonous weed species have been sawn.

The results recorded in Table VI have been collected 21 days after the seeding and the treatment; said results are expressed in percentage of destruction with respect to the non treated plants taken as control.

TABLE VI

| Wettable powder | K | | L | | M | |
|---|---|---|---|---|---|---|
| Doses of butraline (g/ha) | 1000 | 3000 | 1000 | 3000 | 1000 | 3000 |
| % of destruction on | | | | | | |
| Avena fatua | 75 | 95 | 30 | 55 | 20 | 75 |
| Lolium multiflorum | 98 | 100 | 65 | 88 | 70 | 85 |
| Festuca | 93 | 98 | 55 | 85 | 50 | 83 |
| Capsolla bursa-pastoris | 10 | 75 | 0 | 40 | 0 | 40 |
| Stellaria media | 50 | 75 | 45 | 55 | 25 | 70 |

These results show thus the superiority, even in pre-emergence, of the wettable powder according to the invention with respect to powders obtained according conventional processes; this superiority shows a better destruction of weeds, namely of grasses, but also of dicotyledons.

We claim:

1. In a phytopharmaceutical wettable powder comprising at least one pulverulent inert filler and at least one phytopharmaceutical active substance which is solid at ambient temperature and which is selected from the group consisting of:
   the esters of the family of the parahydroxybenzonitriles of the group consisting of bromoxynil octanoate, bromoxynil heptanoate, bromoxynil butyrate, ioxynil octanoate, ioxynil heptanoate, ioxynil butyrate,
   the triazines of the group consisting of simazine, atrazine and ametryne,
   the dinitroanilines of the group consisting of butraline, pendimethaline, trifluraline, orizaline,
   the substituted ureas of the group consisting of diuron, isoproturon, ethidimuron,
   the sulphonylurea consisting of chlorsulfuron, and wherein the particles of the filler constitute a support or carrier for the active substance, the improvement wherein the phytopharmaceutical active substance is comprised within a liquid composition which is obtained by liquefying the phytopharmaceutical active substance by means of a solvent, a liquid active substance, a surfactive agent or by formation of an eutectic with another solid active substance.

2. Phytopharmaceutical wettable powder according to claim 1, wherein the liquid composition is obtained by liquifying the phytopharmaceutical active substance:
   a) by means of a solvent selected from the group consisting of aliphatic, aromatic, cycloaliphatic mineral oils, solvents of petroleum origin, of the alkylaromatic type, plant oils, dimethylformamide, dimethyl sulphoxide, dimethylacetamide, N-methylpyrrolidone, dimethylimidazolinone, hexamethylene-phosphotriamide, cyclohexanone, acetophenone, alcohol diacetone, butylbenzylphthalate, dialkylphthalates, short alcohols with a chain in $C_1$ to $C_8$ and their oxyethylenated and/or oxypropylenated derivates, ethyleneglycol, propyleneglycol, and the solvents on the basis of alkylbenzene and alkylnaphthalene, in which the alkyl chain comprises from 1 to 8 carbon atoms, and/or
   b) by means of a liquid active substance selected from the group consisting, on the one hand, of the phenoxyacids, especially 4- and 3-chlorophenoxyacetic acid, 2.4-D, MCPA, mecoprop and dichlorprop as well as their dextrogyre isomers, in the form of esters of the group comprising those of butylglycol, 2-ethylhexanol, isooctanol and of the alcohols in $C_8$, on the other hand of the fluazifop-P-butyl, metolachlor, pretilachlor, sethoxydime, tebutame, and/or
   c) by means of a surfactive agent selected from the group consisting of:
      non-ionic surface active agents obtained by reaction of ethylene and/or propylene oxide on fatty alcohols, alkylphenols, tristyrylphenols, fatty amides, fatty amines,
      anionic surfactive agents which are the sulphonated, sulphated or phosphorulated derivatives of the above-mentioned non-ionic surfactive agents, possibly neutralized by aliphatic amines, alkanolamines or sodium or potassium hydroxide,
      calcium dodecylbenzenesulphonate, calcium alkylbenzenesulphonates having an alkyl chain in $C_{12}$ to $C_{18}$, sodium or calcium alkylnaphthalenesulphonates, sodium, calcium or ammonium lignosulphonates, formol/cresol/betanaphtholsulphonate condensates and/or
   d) by mixture with a solid active substance proper to form with it an eutectic, the corresponding combination being selected from the group consisting of:
      the combination of bromoxynil octanoate with bromoxynil butyrate, the proportions being respectively 60% and 40% by weight, the melting point being 25° C.,
      the combination of bromoxynil heptanoate with bromoxynil butyrate, the proportions being respectively 70% and 30% by weight, the melting point being 26° C.,
      the combination of bromoxynil octanoate with bromoxynil heptanoate, the proportions being respectively 50% and 50% by weight, the melting point being 26°.

3. Wettable powder according to claim 1 wherein, in the liquid composition, the solvent and/or the liquid active substance selected for liquifying the solid active substance are present in an amount of at most 50% by weight, the surfactive agent being present in a proportion of at most 20% by weight with respect to the total weight of the liquid composition.

4. Wettable powder according to claim 1 wherein, in the liquid composition, the solvent and/or the liquid active substance selected for liquifying the solid active substance are present in an amount of at most 25% by weight, the surfactive agent being present in a proportion of 5 to 10% by weight with respect to the total weight of the liquid composition.

5. Wettable powder according to claim 1, comprising from 1 to 50% by weight of at least one phytopharmaceutical active substances.

6. Wettable powder according to claim 1, comprising from 10 to 25% by weight of at least one phytopharmaceutical active substance.

7. Wettable powder according to claim 1, wherein the inert filler is selected from the group consisting of silica and clays.

8. Wettable powder according to claim 1, wherein the inert filler is selected from the group consisting of those known under the trademarks TIX-O-SIL 38 ® and ARGIREC B 22 ®.

9. Wettable powder according to claim 1, comprising from 30 to 95% by weight with respect to its total weight of at least one pulverulent inert filler selected from the group consisting of silica and clays.

10. Wettable powder according to claim 1, comprising from 30 to 95% by weight with respect to its total weight of at least one pulverulent inert filler selected from the group consisting of those known under the trademarks TIX-O-SIL 38 ® and ARGIREC B 22 ®.

* * * * *